United States Patent [19]

Sebag et al.

[11] 4,105,580

[45] Aug. 8, 1978

[54] POLYGLYCEROL NON-IONIC SURFACE ACTIVE AGENTS AND PROCESS FOR PREPARING THE SAME FROM CRUDE GLYCIDOL

[75] Inventors: Henri Sebag, Paris; Guy Vanlerberghe, Commune de Villevaude, both of France

[73] Assignee: L'Oreal, Paris, France

[21] Appl. No.: 734,367

[22] Filed: Oct. 20, 1976

[30] Foreign Application Priority Data

Oct. 23, 1975 [LU] Luxembourg .......................... 73632

[51] Int. Cl.$^2$ ............................................. B01F 17/22
[52] U.S. Cl. ................... 252/351; 260/609 R; 260/609 B; 260/613 B; 260/613 D; 260/615 R; 260/615 B; 260/561 A; 260/561 B
[58] Field of Search ................... 252/351; 260/615 B, 260/609 R, 609 B, 613 B, 613 D, 615 R, 561 A, 561 B

[56] References Cited

U.S. PATENT DOCUMENTS

| | | | |
|---|---|---|---|
| 3,666,671 | 5/1972 | Kalopissis et al. | 252/351 X |
| 3,719,636 | 3/1973 | Wojtowicz et al. | 260/615 B |
| 3,821,372 | 6/1974 | Vanlerberghe et al. | 260/615 B X |
| 3,879,475 | 4/1975 | Wojtowicz et al. | 252/351 X |
| 3,966,398 | 6/1976 | Vanlerberghe et al. | 260/615 B X |

OTHER PUBLICATIONS

*The Merck Index*, (8th Ed.), 1968, p. 500.

*Primary Examiner*—Leland A. Sebastian
*Assistant Examiner*—E. Suzanne Parr
*Attorney, Agent, or Firm*—Cushman, Darby & Cushman

[57] ABSTRACT

A process for preparing non-ionic surface active agents comprises condensing crude glycidol, in the presence of an alkaline catalyst on an organic compound containing an active hydrogen atom. The crude glycidol is prepared by dehydrochlorinating glycerol monochlorohydrin with sodium or potassium hydroxide in the presence of a solvent, neutralizing excess sodium or potassium hydroxide with a strong acid and separating the major portion of the sodium or potassium chloride formed.

10 Claims, No Drawings

POLYGLYCEROL NON-IONIC SURFACE ACTIVE AGENTS AND PROCESS FOR PREPARING THE SAME FROM CRUDE GLYCIDOL

The present invention relates to a process for preparing water-soluble, polyglycerol non-ionic surface active agents by reacting crude glycidol with certain organic compounds carrying an active hydrogen atom.

Polyglycerol non-ionic surface active agents are known. For instance, French Pat. No. 1.414.048 describes a process for preparing non-ionic surface active agents by polycondensing, in the presence of an alkaline catalyst, glycidol on alkyl phenols.

French Pat. No. 2.091.516 which corresponds essentially to U.S. Pat. Nos. 3,821,372; 3,928,224; 3,966,398 and U.S. application Ser. No. 678,030 and French Pat. No. 2,099,092 which corresponds essentially to U.S. application Ser. No. 563,459 now U.S. Pat. No. 3,984,480 describe the preparation of non-ionic surface active agents by polycondensing, in the presence of an alkaline catalyst, glycidol on, particularly, alkane diols and alkyl mercaptans.

All these processes, however, utilize extremely pure glycidol.

In effect, glycidol, which has the formula

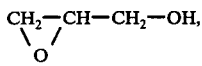

includes in its molecule a hydroxy group and an oxirane group, which groups impart thereto sufficiently strong activity and a marked tendency both to self-polymerize and to form polyglycerols which can interfere with subsequent polycondensation operations.

Pure glycidol is conventionally prepared by dehydrochlorination of glycerol monochlorohydrin using a strong base such as sodium hydroxide or potassium hydroxide, in the presence of a solvent, according to the reaction:

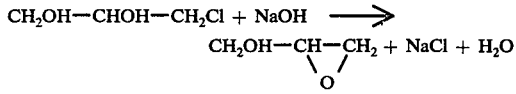

The sodium chloride formed during the reaction is separated by filtration, while the water and solvent employed are distilled.

This process involves numerous disadvantages. In effect, a part of the glycidol is lost by entrainment during distillation of the solvent and water. Moreover, the resulting glycidol has a tendency to self-polymerize on prolonged heating. Additionally, distillation in significant amounts can lead to a non-negligent risk of violent polymerization reaction or even to an explosion.

It has now been found that polyglycerol non-ionic surface active agents can be prepared from crude glycidol, i.e. the glycidol remaining after filtration of the formed sodium chloride, but without separation of the other constituents of the reaction mixture. Thus, the terms crude glycidol solution and crude glycidol mean, in the context of the present invention, the reaction mixture obtained from glycerol monochlorohydrin and containing in addition to the resulting glycidol, the solvent employed, the water formed during the course of the reaction or introduced with the reactants, the fraction of unreacted glycerol monochlorohydrin, small quantities of residual sodium chloride or potassium chloride formed during the course of the reaction and optionally products of hydrolysis or of polymerization of the thus produced glycidol.

This new process overcomes the above stated disadvantages and significantly reduces the cost of preparing the non-ionic surface active agent of the present invention.

The present invention thus relates to a process for preparing polyglycerol non-ionic compounds by reacting, in the presence of a basic catalyst, certain organic compounds containing an active hydrogen with crude glycidol, such as it is obtained by the dehydrochlorination of glycerol monochlorohydrin with a strong base, for example sodium hydroxide or potassium hydroxide, in the presence of an appropriate solvent, after filtration of the major part of the salt formed during the reaction. This process involves two stages. In the first stage, the crude glycidol is prepared from glycerol monochlorohydrin. In the second stage, the resulting crude glycidol which is free from the major part of the salt formed, is polycondensed on certain organic compounds carrying an active hydrogen atom.

It is rather unexpected and surprising to find that to obtain non-ionic surface-active agents of physicochemical properties comparable to those of the compounds described in the patents mentioned above, it is possible to use amounts of crude glycidol substantially equivalent to the amounts of pure glycidol. In fact, during the dehydrochlorination reaction and above all during the polycondensation reaction the glycidol is present under conditions which are entirely favorable for the formation of glycerol or of polyglycerols which contain numerous hydroxyl groups capable of initiating secondary reactions.

As the strong base, sodium hydroxide is preferably employed during the preparation of crude glycidol.

The solvents used for the preparation of crude glycidol in accordance with the invention must meet certain criteria. In particular, they must (1) be solvents for glycerol monochlorhydrin and assure good contact with cold sodium hydroxide without reacting with it, (2) be miscible with water, (3) be a non-solvent for sodium chloride, (4) have a boiling point between 40° and 120° C, and preferably between 60° and 90° C, and of course (5) have the least chemical affinity as possible for the epoxide function. The preferred solvents are tertio-butanol and especially isopropanol. The weight ratio of solvent to glycerol monochlorhydrin is from 1 to 3 and preferably equal to 2.

The dehydrochlorination reaction is effected by adding NaOH to the mixture of glycerol chlorohydrin and solvent. The NaOH can be added in stoichiometric proportions in the form of flakes, or preferably in powder form, or even as a 40 or 50% aqueous solution. Since the reaction is exothermic, the temperature must be maintained between 10° and 35° C, and preferably between 15° and 20° C.

The reaction is relatively very rapid since the addition of NaOH lasts from 15 minutes to 1 hour, and preferably from 15 to 30 minutes. The reaction is considered terminated 30 minutes following the NaOH addition operation.

The reaction medium is neutralized by the addition of a sufficient quantity of HCl diluted 3, 4 or 5 times with solvent. Thereafter the salt formed, for instance, sodium chloride, is rapidly filtered therefrom and the remaining reaction mixture is dried and rinsed.

The strength and yield of oxirane groups are determined by dosage of the filtrate. The yield is generally between 75 and 95%.

It is important to determine the amount of glycerol monohydrochlorine remaining in the crude glycidol solution for it enters into the calculation of quantities of the basic catalyst that are introduced during the polyaddition operation.

The quantity of glycerol monochlorohydrin remaining is generally between 0 and 5% but can reach 10% without encountering any prejudicial consequences relative to the properties of the resulting non-ionic surface active agents.

The second stage of the process of the present invention includes the condensation of the crude glycidol on an organic compound or a mixture of organic compounds containing an active hydrogen atom in the presence of a basic catalyst.

Initially, the organic compound containing an active hydrogen atom is heated with the basic catalyst, under a nitrogen atmosphere, up to a temperature of about 150°–155° C. Then the crude glycidol solution is slowly added while maintaining the temperature at about 150°–155° C and while distilling off the solvent and water. The addition of the crude glycidol generally lasts between about 1 hour and 3 hours.

The reaction mixture is then cooled to about 100°–120° C after which the apparatus containing the same is placed under reduced pressure for a few minutes to remove the last traces of solvent.

As the basic catalyst, there is employed, preferably, sodium methylate, sodium hydroxide or potassium hydroxide.

The quantity of catalyst used for the condensation reaction is generally from 0.02 to 0.15 mole per mole of organic compound having the active hydrogen atom, which amount is augmented or increased by an amount necessary to react with the unreacted glycerol monochlorohydrin remaining in the crude glycidol solution.

For each mole of unreacted glycerol monochlorohydrin present in the crude glycidol solution, it is necessary to add one mole of basic catalyst.

Since the quantity of unreacted glycerol monochlorohydrin remaining in the crude glycidol solution is usually from 0 to 0.1 mole and more generally from 0 to 0.05 mole per mole of glycidol present in the solution, the total quantity of catalyst to use for the condensation reaction is from 0.02 to 0.15 mole per mole of organic compound having the active hydrogen atom, increased or augmented by from 0 to 0.1 and more frequently from 0 to 0.05 mole per mole of glycidol.

The organic compounds having an active hydrogen atom usefully employed in the process of the present invention are selected from the group consisting of:

(a) alkyl mercaptans having the formula $R_1SH$ where $R_1$ is alkyl having from 8 to 18 carbon atoms;

(b) glycerol alkyl thioethers having the formula $R_1$—S—$CH_2$—CHOH—$CH_2OH$ wherein $R_1$ has the same meaning given in (a) above;

(c) alkyl phenols of the formula

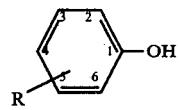

and glycerol alkyl phenyl ethers of the formula

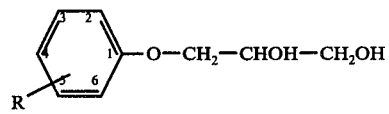

where one of the carbon atoms in 2 and 4 positions is linked to an alkyl radical having 8 to 18 carbon atoms, the other generally being linked to a hydrogen atom or occasionally to a second alkyl radical having up to 18 carbon atoms and preferably 1–8 carbon atoms.

Representative examples of the alkyl phenyl radical

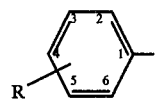

in either of the above include:

p-isononylphenyl, p-isododecylphenyl, p-tertoctylphenyl, p-sec-octylphenyl, p-sec-dodecylphenyl, and their mixtures;

(d) 1,2-α-diols of the formula $R_2$—CHOH—$CH_2OH$ wherein $R_2$ represents (i) a straight chain alkyl having 6 to 16 carbon atoms or a mixture of several of these radicals;

(ii) a radical or a mixture of radicals selected from the following group:
$R_3$—CHOH—$CH_2$—S—$CH_2$—,
$R_3$—CHOH—$CH_2$—O—$CH_2$— and

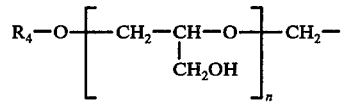

wherein $R_3$ and $R_4$ represent an alkyl radical or a mixture of alkyl radicals, having from 8 to 18 carbon atoms, $R_4$ also being able to be a mixture of alicyclic and aliphatic radicals having up to 30 carbon atoms and being derived from lanolin alcohols, and $n$ represents a whole or decimal number from 0 to 2, said number representing a definite value or a statistical average value;

(e) fatty acid diglycolamides of the formula

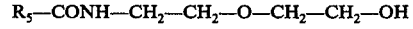

where $R_5$ represents an alkyl or alkenyl radical or a mixture thereof having from 7 to 17 carbon atoms. For those diglycolamides which have a tendency to partially hydrolyze, it is preferable to use sodium hydroxide in a non-aqueous form during the preparation of the crude glycidol and to progressively introduce the catalyst by fractions into the reaction mixture during the second stage of the process.

When an alkyl mercaptan or a glycerol thio ether alcohol is employed as the organic compound having an active hydrogen atom, the non-ionic agent obtained after the condensation of the crude glycidol can be oxidized to sulfoxide form.

Generally from 1 to 10 moles of glycidol are condensed per mole of organic compound, although more than 10 moles of glycidol can be employed.

The present invention also relates to new compounds which are non-ionic surface active agents obtained by the reaction of 1-10 moles of crude glycidol per mole of a compound of the formula

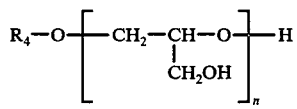

where $R_4$ represents an alkyl radical or a mixture of alkyl radicals, having from 8 to 18 and preferably from 12 to 18 carbon atoms or a mixture of aliphatic and alicyclic radicals having up to 30 carbon atoms and being derived from lanolin alcohols, and $n$ represents a whole or decimal number from 0 to 3, and preferably from 1 to 3, said number representing a definite value or a statistical average value.

Those new non-ionic surface active agents are compounds of formula:

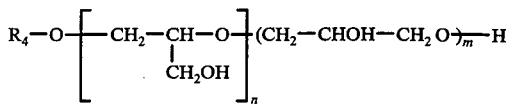

where $R_4$ represents an alkyl radical or a mixture of alkyl radicals, having from 8 to 18 and preferably from 12 to 18 carbon atoms or a mixture of aliphatic and alicyclic radicals having up to 30 carbon atoms and being derived from lanolin alcohols, $n$ represents a whole or decimal number from 0 to 3, and preferably from 1 to 3, said number representing a definite value or a statistical average value, and $m$ represents a whole or decimal number from 1 to 10. These are surfactants, and as the case may be, they are foaming agents, softeners, thickeners, peptizers or emulsifiers.

The non-ionic surface active agents obtained in accordance with the present case have properties or characteristics which are essentially the same as for the surface active agents described in French Pat. Nos. 2,091,516 and 2,099,092 and their respective U.S. counterparts as noted above. These characteristics are a function of the number of moles of glycidol added per mole of organic compound having an active hydrogen atom. However, the surface active agents obtained in accordance with the present invention exhibit, relative to those prepared in accordance with said known procedures, the unexpected advantage of having substantially less color. This advantage can be quite important especially when these products are employed in cosmetic or pharmaceutical compositions.

The present invention is illustrated by the following nonlimiting examples:

EXAMPLE A

Preparation of a crude glycidol solution with powdered sodium hydroxide

To 331.5 g (3 moles) of glycerol monochlorohydrin, there are added 500 g of isopropanol. Thereafter, over a 20 minute period, 120 g (3 moles) of powdered NaOH are added to the resulting solution.

The ensuing reaction is exothermic and so the reaction mixture is cooled with an ice water bath so as to maintain the temperature thereof between 15° and 20° C.

One half hour after the last of the NaOH has been added, the remaining NaOH in the reaction mixture is neutralized with 2 ml of HCl diluted 5 times with isopropanol. The sodium chloride which forms is then rapidly filtered.

After filtering and rinsing with 100 g of isopropanol, 730 g of crude glycidol solution are obtained wherein the content of oxirane groups is 3.3 meq/g, i.e. the yield of oxirane groups is 81%. Organic chloride index = 0.1 meq/g; ionized chloride index = 0.04 meq/g.

EXAMPLE B

Preparation of a crude glycidol solution with aqueous NaOH

As in Example A, 331.5 g (3 moles) of glycerol monochlorohydrin are admixed with 500 g of isopropanol.

To the resulting mixture, over a 20 minute period and at a temperature between 15° and 20° C, 240 g (3 moles) of a 50% aqueous solution of NaOH are added thereto.

30 minutes later and at a temperature of 20° C, the reaction mixture is neutralized with 2.5 ml of HCl diluted 5 times with isopropanol. The reaction mixture is then filtered and rinsed with 100 g of isopropanol, yielding 980 g of solution whose content of oxirane groups is 2.8 meq/g, i.e. the yield of oxirane groups is 91.5%. Organic chloride index = 0.09 meq/g; ionized chloride index − 0.28 meq/g.

EXAMPLE 1

Polyaddition of crude glycidol on 1,2-dodecane diol

To 21 g (0.1 mole) of 1,2-dodecane diol having the formula $C_{10}H_{21}$—CHOH—$CH_2$OH, there are added 2.5 g (0.012 mole) of sodium methylate in solution in methanol.

The resulting mixture is heated under a nitrogen atmosphere to 150°-155° C in an apparatus fitted with an ordinary condenser. Over a 75 minute period there are added thereto 91 g of the crude glycidol solution obtained in Example A (0.3 mole), while distilling off the isopropanol and the water.

The last traces of solvent are removed by heating the reaction mixture for 5 minutes at 120° C under reduced pressure.

A light brown product, soluble in water and in 40% NaOH, is thus obtained. This product can have the following formula:

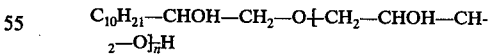

wherein $n$ represents a statistical average value of 3.

The cloud point of the product measured at a concentration of 0.5% is greater than 100° C in demineralized water and is 95° C in water containing 10% NaCl.

EXAMPLE 2

Polyaddition of glycidol on a mixture of essentially $C_{15}$ to $C_{18}$ alkanediols To 20 g of Adol 158 (0.075 mole) sold by Ashland Chemicals, 2.3 g of a methanolic solution of sodium methylate (0.011 mole), are added. The resulting mixture is heated to a temperature of 150°–155° C, under a nitrogen atmosphere, and at this temperature 91 g of the crude glycidol solution obtained in Example A (0.3 mole) are added with the solvents continuously being removed by an ordinary condenser. The duration of the glycidol addition is 1½ hours.

After cooling the reaction mixture to 120° C, the reaction is terminated by placing the reaction apparatus under reduced pressure for about 5 minutes.

There is thus obtained a light brown surface active agent soluble in water and in 40% NaOH. Its Kraft point measured at a concentration of 1% is 22° C.

Its cloud point at 0.5% is greater than 100° C in demineralized water and in water containing 10% NaCl.

Adol 158 contains a mixture of 1,2-alkane diols of the formula $R_2$—CHOH—$CH_2OH$ where $R_2$ represents a mixture of alkyl radicals having the following chain lengths in the following proportions:

$C_{11}$ — 0.9%; $C_{12}$ — 1.3%; $C_{13}$ — 30%; $C_{14}$ — 32.4%; $C_{15}$ — 23.2% and $C_{16}$ — 12.2% = 100%

The resulting surface active agent can have the following formula:

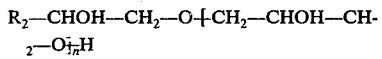

where $R_2$ has the meaning given above and $n$ has a statistical average value of 4.

EXAMPLE 3

Polyaddition of glycidol with lauryl mercaptan

To 20.2 g of lauryl mercaptan (0.1 mole) having the formula $C_{12}H_{25}SH$, 2.2 g of a methanolic solution of sodium methylate (0.011 mole) are added under a nitrogen atmosphere. The resulting mixture is heated to a temperature of 60°–70° C, at which temperature and over a 25 minute period 30 g (0.1 mole) of the crude glycidol solution obtained in Example A are added thereto. This mixture is then heated to a temperature of 150°–155° C and the solvents are distilled off while an additional 45.5 g of the crude glycidol solution (0.15 mole) are added thereto. The duration of the glycidol addition lasts 45 minutes.

There is thus obtained a surface active agent having a light yellow color which is dispersible in water and which can have the following formula:

wherein $n$ represents a statistical average value of 2.5.

The above product is then oxidized to the sulfoxide form by the addition thereto of 5.7 ml of $H_2O_2$ (195 volumes — 0.1 mole) diluted to 10 ml with water in the presence of 0.5 ml of acetic acid.

A white pasty product which is soluble in water is obtained. Its Kraft point is 14° C. Its cloud point is greater than 100° C in demineralized water and in water containing 10% NaCl.

EXAMPLE 4

Polyaddition of glycidol on isononylphenol

To 22 g of isononylphenol (0.1 mole) of the formula $C_9H_{19}$—$C_6H_4OH$, there are added 5 g of sodium methylate in a methanolic liquor (0.025 mole). There are then added, under a nitrogen atmosphere and at a temperature of 155° C, 150 g of a crude glycidol solution (0.5 mole) obtained in accordance with Example A. The duration of the glycidol addition is 2 hours.

The solvents are completely removed from the reaction mixture by placing the apparatus containing the same under reduced pressure for 5 minutes at 120° C.

A surface active agent in the form of a brown colored paste is obtained which is soluble in water and in 40% NaOH. The product can have the following formula

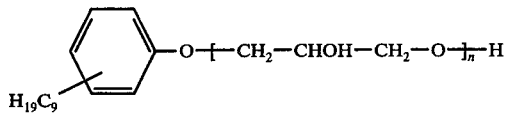

wherein $n$ represents a statistical average value of 5.

The characteristics of this surface active agent are as follows: its Kraft point is lower than 0° C; its cloud point in water is greater than 100° C; and its cloud point in water containing 10% NaCl is 60° C.

EXAMPLE 5

Polyaddition of glycidol on copra diglycolamides of the formula $R_5$—CONH—$CH_2$—$CH_2$—O—$CH_2$—$CH_2$—OH;
$R_5$—COOH representing copra fatty acids To 30 g of a mixture of the above amides (0.1 mole), 10 ml of a methanolic liquor of sodium methylate (0.021 mole) are added in four fractions, alternately with 90 g of a crude glycidol solution obtained in accordance with Example A (0.3 mole), the latter also being portioned out in four fractions. Thus, in accordance with this scheme, there are initially introduced 2 ml of sodium methylate, then 22.5 g of the crude glycidol solution, then 2 ml of sodium methylate followed by 22.5 g of glycidol solution, until the four fractions of each have been introduced.

The addition of the crude glycidol solution lasts 1 hour. After essentially complete removal of the solvents, a surface active agent having a light brown color is obtained which is soluble in water. This product can have the following formula:

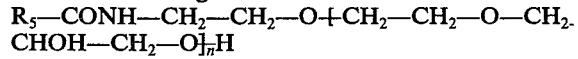

wherein $R_5$ has the meaning indicated above, and $n$ represents a statistical average value of 3. Its cloud point in demineralized water is greater than 100° C and its cloud point in water containing 10% NaCl is 28° C.

EXAMPLE 6

Polyaddition of glycidol on $C_{12}$ and $C_{14}$ alkanediols

To 31.5 g (0.15 mole) of a 50/50 $C_{12}$ and $C_{14}$ alkane diol mixture, there are added 5 g of an aqueous solution of NaOH (0.025 mole). Thereafter, under a nitrogen atmosphere and at a temperature of 155° C, 187 g of a crude glycidol solution obtained in accordance with Example B (0.525 mole) are added thereto. The solvents are removed as in the preceding examples and there is obtained a surface active agent having a light brown color which is soluble in water and 40% NaOH and which can have the following formula:

wherein $R_2$ represents a 1:1 mixture of $C_{10}$ and $C_{12}$ alkyls and $n$ represents a statistical average value of 3.5. Its cloud point determined in demineralized water and in water containing 10% NaCl is greater than 100° C.

EXAMPLE 7

Polyaddition of glycidol on a polyhydroxylated non-ionic compound of the formula:

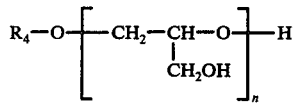

wherein $R_4$ is a mixture of $C_{16}H_{33}$ and $C_{18}H_{37}$ in a proportion of about 50/50, and $n$ represents a statistical average value of 2.

To 71 g (0.15 mole) of the above non-ionic compound, which can be prepared as described in Ser. No. 846.929, now U.S. Pat. No. 3,666,671 and U.S. Pat. No. 3,578,719. 5 g of an aqueous NaOH solution (0.025 mole) are added thereto. Then at 155° C and under a nitrogen atmosphere, 213 g (0.6 mole) of a crude glycidol solution obtained as in Example B are added. The solvents are removed as in the preceding examples. There is thus obtained a hard paste having a light brown color which is soluble in water and in 40% NaOH. Its Kraft point is lower than 0° C. Its cloud point is greater than 100° C in demineralized water and in water containing 10% NaCl.

The compound thus obtained has the formula:

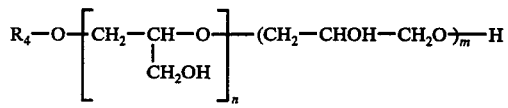

wherein $m = 4$, and $R_4$ and $n$ have the meaning indicated above.

EXAMPLE 8

Polyaddition of 4 moles of glycidol per mole of a polyhydroxylated non-ionic compound of the formula:

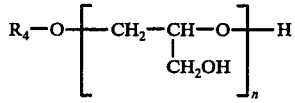

wherein $R_4$ represents a mixture of aliphatic and alicyclic radicals derived from lanolin alcohols, and $n$ represents a statistical average value of 2.

To 155 g of the above non-ionic compound (750 meq in hydroxyl groups) which can be prepared in accordance with the process described in U.S. Pat. Nos. 3,578,719; 3,666,671; 3,865,542 and 3,877,955, there are added at a temperature of 155° C and under a nitrogen atmosphere, 9.7 g of a NaOH solution (10.1 meq/g). Thereafter, there are added slowly 327 g (1000 meq) of a crude glycidol solution prepared according to the procedure of Example B, said solution having an epoxide index of 2.87 meq/g and an organic chloride index of 0.18 meq/g.

There is thus obtained a very hard paste having a light brown color soluble in water with a very slight opalescence and having a cloud point in water containing 10% NaCl greater than 100° C.

The compound thus obtained has the formula:

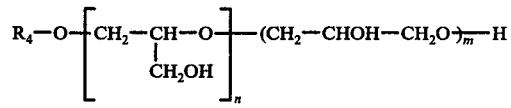

where $m = 4$ and $R_4$ and $n$ have the meaning indicated above.

EXAMPLE 9

Polyaddition of 2 moles of glycidol per mole of a polyhydroxylated non-ionic compound of the formula:

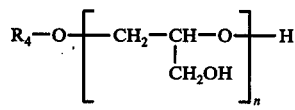

where $R_4$ represents a mixture of $C_{12}H_{25}$ and $C_{14}H_{29}$ radicals in a ratio of about 55/45, and $n$ has a statistical average value of 1.5 prepared in accordance with the procedure of Ser. No. 846,929, now U.S. Pat. No. 3,666,671 and U.S. Pat. No. 3,578,719.

To 76 g of the above non-ionic compound (520 meq in hydroxyl groups) there are added 4.5 g of NaOH (10.1 meq/g). Then at a temperature of 155° C and under a nitrogen atmosphere, 164 g of a crude glycidol solution which is essentially the same as that employed in Example 8 are slowly added. The solvents are removed in a manner essentially as outlined in Example 1 above.

There is thus obtained a light brown color paste which is soluble in water. Its cloud point in demineralized water is greater than 150° C and it is 47° C in water containing 10% NaCl.

The compound thus obtained has the formula:

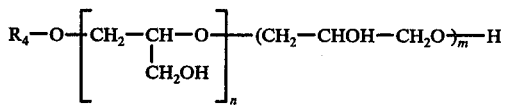

where $m = 2$ and $R_4$ and $n$ have the meaning indicated above.

What is claimed is:

1. A two stage process for preparing a water-soluble non-ionic surface active agent comprising, in a first stage (a) reacting glycerol monochlorohydrin with a strong base in the presence of a solvent at a temperature between 10° and 35° C for a period ranging from 15 minutes to 1 hour to produce a solution of crude glycidol; (b) neutralizing the said solution of crude glycidol with a strong acid whereby a salt is formed, separating a major portion of the thus formed salt from the said solution of crude glycidol, the said solution of crude glycidol containing from 0 to 0.1 mole of unreacted glycerol monochlorohydrin per mole of glycidol present in said solution; and in a second stage (c) condensing the said solution of crude glycidol resulting from step (b) with an organic compound containing an active hydrogen in the presence of an effective amount of an alkaline catalyst to produce said non-ionic surface active agent, said organic compound being selected from the group consisting of (1) alkyl mercaptan having the formula $R_1SH$ wherein $R_1$ represents alkyl having from 8 to 18 carbon atoms, (2) glycerol alkyl thioether having the formula $R_1$—S—$CH_2$—CHOH—$CH_2OH$ wherein $R_1$ represents alkyl having from 8 to 18 carbon atoms, (3) alkyl phenol having the formula

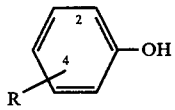

or glycerol alkyl phenyl ether having the formula

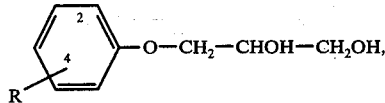

wherein one of the carbon atoms in the 2- and 4- positions is linked to R wherein R is alkyl having from 8 to 18 carbon atoms and the other of said carbon atoms is linked to a member selected from the group consisting of alkyl having from 1–8 carbon atoms and hydrogen, (4) 1,2-α-diol of the formula $R_2$-CHOH-$CH_2OH$ wherein $R_2$ is selected from the group consisting of (i) straight chain alkyl having 6–16 carbon atoms or a mixture thereof, (ii) $R_3$-CHOH-S-$CH_2$-, (iii) $R_3$-CHOH-$CH_2$-O-$CH_2$-,

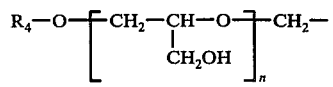

(v) a mixture of (ii) to (iv), wherein $R_3$ represents alkyl having 8–18 carbon atoms or a mixture thereof, $R_4$ represents a member selected from the group consisting of alkyl having 8–18 carbon atoms or a mixture thereof and a mixture of aliphatic and alicyclic radicals having up to 30 carbon atoms and being derived from lanolin alcohols, and $n$ represents a whole or decimal number from 0 to 2, said number representing a definite value or a statistical average value, and (5) fatty acid diglycolamide having the formula $R_5$—CONH—$CH_2$—$CH_2$—O—$CH_2$—$CH_2OH$ wherein $R_5$ represents alkyl or alkenyl having 7–17 carbon atoms or a mixture thereof.

2. The process of claim 1 wherein said solvent is selected from the group consisting of isopropanol and tert-butanol.

3. The process of claim 2 wherein said solvent is isopropanol.

4. The process of claim 1 wherein the strong base reacted with glycerol monochlorohydrin is sodium hydroxide in the form of a powder, flakes or a 40–50% aqueous solution in stoichiometric quantities.

5. The process of claim 1 wherein said strong acid is hydrochloric acid.

6. The process of claim 1 wherein said alkaline catalyst is sodium methylate, sodium hydroxide or potassium hydroxide.

7. The process of claim 1 wherein said alkaline catalyst is present in an amount of 0.02 to 0.15 mole per mole of said organic compound containing an active hydrogen with the proviso that when said solution of crude glycidol contains unreacted glycerol monochlorohydrin the amount of catalyst is increased by 1 mole per mole of unreacted glycerol monochlorohydrin present in said solution of crude glycidol.

8. A non-ionic surface active agent prepared in accordance with the two stage process of claim 1.

9. A non-ionic surface active agent which is the reaction product of 1–10 moles of crude glycidol per mole of compound having the formula

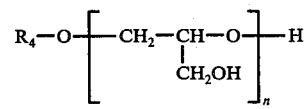

wherein $R_4$ represents a member selected from the group consisting of alkyl having 8–18 carbon atoms or a mixture thereof and a mixture of aliphatic and alicyclic radicals having up to 30 carbon atoms and being derived from lanolin alcohols, and $n$ represents a whole or decimal number from 1 to 3, said number representing a definite value or a statistical average value.

10. A non-ionic surface active agent of formula:

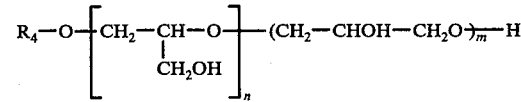

wherein $R_4$ represents a member selected from the group consisting of alkyl having 8–18 carbon atoms or a mixture thereof and a mixture of aliphatic or alicyclic radicals having up to 30 carbon atoms and being derived from lanolin alcohols, and $n$ represents a whole or decimal number from 1 to 3, said number representing a definite value or a statistical average value, and $m$ represents a whole or decimal number from 1 to 10.

* * * * *